US006495537B1

(12) United States Patent
Jacobson et al.

(10) Patent No.: US 6,495,537 B1
(45) Date of Patent: Dec. 17, 2002

(54) METHOD FOR INHIBITION OF PHOTOCARCINOGENESIS OR PHOTOIMMUNOSUPPRESSION USING NIACIN

(75) Inventors: Elaine L. Jacobson, Tucson, AZ (US); Helen L. Gensler, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/452,745

(22) Filed: Dec. 1, 1999

(Under 37 CFR 1.47)

Related U.S. Application Data

(60) Provisional application No. 60/110,483, filed on Dec. 1, 1998.

(51) Int. Cl.⁷ ........................ A61K 31/33; A61K 31/455
(52) U.S. Cl. ........................ 514/183; 514/844; 514/846; 424/59; 424/401
(58) Field of Search .................. 424/59, 401; 514/846, 514/844, 183

(56) References Cited

U.S. PATENT DOCUMENTS

| | | |
|---|---|---|
| 5,496,827 A | 3/1996 | Patrick |
| 5,582,817 A | * 12/1996 | Otsu et al. |
| 5,747,049 A | * 5/1998 | Tominaga |

FOREIGN PATENT DOCUMENTS

| | | |
|---|---|---|
| JP | 08301760 | 11/1996 |

OTHER PUBLICATIONS

Ludwig et al., Cancer Research, vol. 50, pp. 2470–2475, Apr. 15, 1990.*

Helen L. Gensler et al., Oral Niacin Prevents Photocarcinogenesis and Photoimmunosuppression in Mice, Nutrition and Cancer, 34(1), 36–41 (1999).

Jacobson et al., "Chemoprevention by niacin in a mouse modelof uv–induced skin carcinogenesis" Proc. Annu Meet Am Assoc Cancer Res; 37:1900 (1996) (meeting abstract).

Helen L. Gensler, Prevention of Photoimmunosuppression and Photocarcinogenesis by Topical Nicotinamide, Nutrition and Cancer, 29(2), 157–162 (1997).

E.L. Jacobson and M.K. Jacobson, A biomarker for the assessment of niacin nutriture as a potential preventive factor in carcinogenesis, Journal of Internal Medicine, 223: 59–62 (1993).

Database Dissertation Abstracts Online, Modulation of carcinogenic process by niacin status, vol. 59, No. 03–B, p. 1050 (1997).

* cited by examiner

Primary Examiner—James O. Wilson
(74) Attorney, Agent, or Firm—Fulbright & Jaworski LLP.

(57) ABSTRACT

The invention is directed to novel methods for the suppression of photocarcinogenesis and photoimmunosuppression in mice. The novel methods comprises the step of administering to a subject a pharmaceutical composition comprising niacin and a pharmaceutical carrier.

10 Claims, 3 Drawing Sheets

METHOD FOR INHIBITION OF PHOTOCARCINOGENESIS OR PHOTOIMMUNOSUPPRESSION USING NIACIN

CROSS REFERENCE TO RELATED APPLICATIONS

This application claims benefit of provisional patent application Ser. No. 60/110,483 filed Dec. 1, 1998. The entire disclosure of provisional patent application Ser. No. 60/110,483 is hereby incorporated by reference.

BACKGROUND

1. Field of the Invention

This invention is directed to methods and compositions for the oral administration of niacin for the prevention of photocarcinogenesis and photoimmunosuppression.

2. Description of the Background

Nonmelanoma skin cancers are the most frequent of human cancers, approximating 62.5% of the expected incidence for all non-skin cancers combined (Parker, S L et al., *CA Cancer J Clin* 47, 5–27, 1997). Nonmelanoma skin cancers have been increasing in incidence at an annual rate of 3–6% (Gallagher, R P et al., *J Am Acad Dermatol* 23, 413–421, 1990). The increase in nonmelanoma skin cancer rate is likely due to an increase in lifetime exposure to UV radiation caused by a longer life expectancy and ozone depletion (Moseley, H, and Mackie, R M, *Brit J Dermatol* 137, 101–103, 1997). Nonmelanoma skin cancers represent considerable morbidity (Johnson M L et al., *J Am Acad Dermatol* 11: 930–936, 1984). Both squamous cell carcinoma and basal cell carcinoma can be invasive and tend to present as multiple primary tumors on visible areas of the body (Kwa, R E, et al., *J Am Acad Dermatol* 26, 1–26, 1992; Miller, S J, *J Am Acad Dermatol* 24, 1–13, 1991; Miller, S J, *J Am Acad Dermatol* 24, 161–175, 1991; Schreiber, M M, *J Am Acad Dermatol* 23, 1114–1118, 1990). The use of sunscreens alone may not be sufficient protection against skin cancer development (Naylor, M F et al., *Arch Dermatol* 131, 170–175, 1995). These observations indicate an increasing need for novel skin cancer prevention strategies.

SUMMARY OF THE INVENTION

It is an object of the invention to suppress or reverse photoimmunosuppression and photocarcinogenesis in a subject.

One embodiment of the invention is directed to a method for reducing photocarcinogenesis or photoimmunosuppression in a subject. In the method, one or more oral administration of a pharmaceutical composition is given to the subject. The pharmaceutical composition comprises niacin in an amount effective to reduce photocarcinogenesis or photoimmunosuppression. The pharmaceutical composition may optionally comprise a pharmaceutically acceptable carrier. The method may be used to reduce, eliminate, prevent or reverse photocarcinogenesis. Further, the method may be used to reduce, eliminate, prevent or reverse photoimmunosuppression.

The subject to be treated may be any animal. Thus, the subject may be a mammal, such as, for example, a human.

The pharmaceutical composition may contain niacin in an amount such that the dosage to be administered orally is between 1 mg niacin per kilogram of subject weight to about 100 mg per kilogram of subject weight. Preferably, the dosage is between 10 mg niacin per kilogram of subject weight to about 40 mg per kilogram of subject weight.

The photoimmunusuppression and photocarcinogenesis referred to in this application may be caused by natural or artificial means. Natural means include direct or reflected sunlight. Artificial means include all man made ultraviolet light sources such as UV lamps, residue UV from lighting fixtures, and ultraviolet light emitted from industrial processes and methods of manufacture.

DESCRIPTION OF THE INVENTION

Figure 1A:
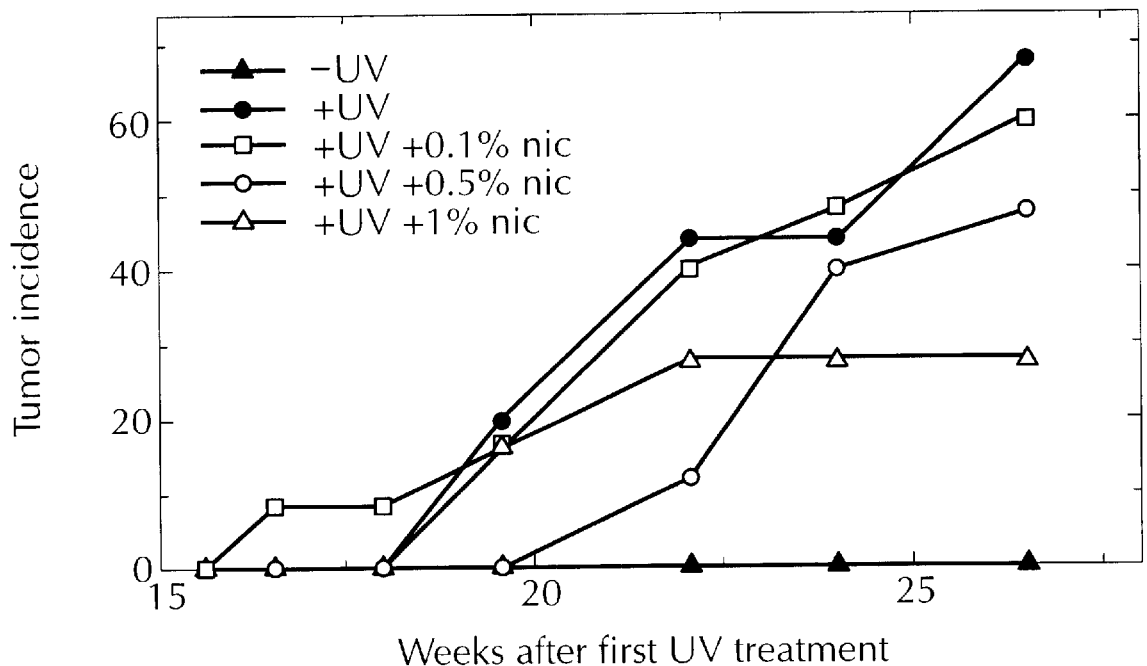
FIG. 1 depicts (A) the rate of tumor development in UVB/A irradiated mice treated with a diet of 0, 0.1, 0.5 or 1.0% niacin throughout the study and (B) tumor multiplicity in UV-irradiated mice treated with niacin supplementation. Values are means +/−SEM.

As discussed above, ultraviolet irradiation can cause photocarcinogenesis and photoimmunosuppression in humans. Current methods of preventing photocarcinogenesis and photoimmunosuppression involve the use of sunblocks. Sunblock (i.e., sunscreen) refers to any chemical that when applied to the skin, reduces the amount of UV light that reaches the skin. By preventing UV absorptions, sunblocks can prevent photocarcinogenesis and photoimmunosuppression. Sunblocks were originally designed to prevent sunburn (also known as erythema), an acute reaction to overexposure to the sun. The strength of sunblocks is measured by the SPF index (Sun Protection Factor). An SPF value of 15, for example, will provide 15 times the protection of bare skin to sunburns. However, sunblocks are disadvantageous because they require frequent application to the skin. Further, every major class of sunblock has been linked to skin allergies.

To overcome the disadvantages of the current methods, experiments were performed to determine if niacin, administered orally, can decrease photoimmunosuppression and photocarcinogenesis.

One embodiment of the invention is directed to a method for reducing photocarcinogenesis or photoimmunosuppression in a subject. The subject can be any animal, such as a mammal. Preferably, the mammal is a human. In the method, a pharmaceutical composition comprising niacin in an amount effective to reduce photocarcinogenesis or photoimmunosuppression is administered orally to the subject. The method can reduce, eliminate, prevent or reverse photocarcinogenesis or photoimmunosuppression.

In a preferred embodiment, the administration comprises oral dosages of about 1 mg to about 100 mg per kilogram of subject weight. Preferably, the oral dosage is between about 10 mg to about 40 mg per kilogram of subject weight.

The niacin may be administered with a pharmaceutically acceptable carrier. The pharmaceutically acceptable carrier may be any carrier known in the field as suitable for pharmaceutical oral application. Suitable pharmaceutical carriers and formulations are described, for example, in Remington's Pharmaceutical Sciences (19th ed.) (Genarro, ed. (1995) Mack Publishing Co., Easton, Pa.).

In addition, niacin and the pharmaceutically acceptable carrier may be enclosed in a hard or soft shell gelatin capsule, compressed into tablets, or incorporated directly into the individual's diet. Specifically, niacin may be incorporated with excipients and used in the form of ingestible tablets, buccal tablets, troches, capsules, elixirs, suspensions, syrups, wafers, and the like. When niacin is administered orally, it may be mixed with other food forms and pharmaceutically acceptable flavor enhancers. When the niacin agent is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are known in the art and also contemplated.

It is understood that the photocarcinogenesis or photoimmunosuppression referred to in this application may refer to any carcinogenesis or immunosuppression caused by light. The light may be, for example, from natural sources such as sunlight or from manmade sources such as a broad spectrum light source, a narrowband UV source, UVA source, UVB source, or UVC source.

Other embodiments and advantages of the invention are set forth, in part, in the description which follows and, in part, will be obvious from this description and understood by the skilled artisan practicing this invention.

EXAMPLE 1
Administration of Niacin

Six-week-old specific-pathogen-free female BALB/cAnNTacfBR ($H-2^d$) mice were purchased from Taconic Laboratory Animals (Germantown, N.Y.) and quarantined from two weeks before treatment. Animals were housed in microisolators under barrier conditions with a 12:12-hour light-dark cycle at 20+/−2° C. (SD).

Groups of 25 mice each received the basal diet which consisted of the American Institute of Nutrition 76A rodent diet containing 10% corn oil and 30 mg niacin per kilogram diet, supplemented with 0, 0.1, 0.5, or 1.0% niacin (Dyets Inc. Bethlehem, Pa.). All diets were pelleted (Dyets Inc.) without heat or steam and stored under refrigeration for less than 10 weeks. Animals were fed ad libitum and given fresh diet three times per week for three weeks before UV treatments began, and throughout the study. Niacin intakes were calculated from the diet consumed. Animals were supplied with sterilized water ad libitum.

EXAMPLE 2
UV Irradiation

The mice were exposed to UV radiation after three weeks of oral niacin administration. The animals were shaved dorsally with animal clippers each week. The filter tops, food, and water bottles were removed from the microisolators while mice were exposed to UV radiation emitted by banks of six FS40 Westinghouse fluorescent sun lamps for 30 min per day, five days per week. This UV regimen continued for 22 weeks in the carcinogenesis experiments, and for 11 weeks in the passive transfer assay experiments. The cages were systemically rotated during the study to compensate for any differences in flux at different positions under the lamps. The FS40 lamps emit a continuous spectrum from 270 to 390 nm with peak emission at 313 nm. About 75% of the energy output is in the wavelength range of 280–340 nm with about 23% in the 340–390 nm range. The total UVB radiation dose was approximately $1.41 \times 10^6$ $Jm^{-2}$ in the carcinogenesis experiments, and about $0.705 \times 10^5$ $Jm^{-2}$ in the passive transfer experiments, as measured with a UVX Digital Radiometer with a UVX-31 sensor (Ultraviolet Products, San Gabriel, Calif.).

EXAMPLE 3
Passive Transfer Assay

The passive transfer assay determines photoimmunosuppression by measuring the capacity of a mouse to reject antigenic, syngeneic tumors. This assay has been described previously (Gensler, H L, Nutr Cancer 29, 157–162, 1997; Gensler, H L, J Cancer Res Clin Oncol 117, 345–350, 1991; Gensler, H L, Nutr Cancer 22, 121–130, 1994). Briefly, spleens were excised under aseptic conditions from mice after 11 weeks of UVB treatment. A total of 15 mice per group was used for analysis. The groups consist of (1) the 0% niacin diet group, (2) the 0.1% niacin diet group, (3) the 0.5% niacin diet group, and (4) the 1.0% niacin diet group. Spleen cells isolated from the spleens were triturated with RPMI 1640 medium without fetal bovine serum, washed, and resuspended in fresh medium. Splenocytes were injected into the lateral tail veins of 15 naive mice per treatment group. Within 24 hours, recipients were challenged with about $5 \times 10^5$ UVM12 (syngeneic antigenic UV-induced) tumor cells injected intradermally into the flanks. Tumor growth was measured twice weekly with vernier calipers.

EXAMPLE 4
Tissue Extraction and Assay

Dorsal and ventral skin samples were excised from mice at 29.5 weeks after niacin supplementation began. Samples were immediately frozen in liquid nitrogen and stored at −80° C. For nicotinamnide-adenine-dinucleotide (NAD) and protein analyses, the tissue was ground to a fine powder in liquid nitrogen by mortar and pestle. The powder was then transferred to a 15 ml centrifuge tube containing 1 ml of 1 M NaOH. This mixture was rapidly neutralized with 0.27 ml of 2 M $H_3PO_4$, so that total time in alkali was less than 2 min. Next, 0.13 ml of 2 M phenazine ethosulfate was added to convert NADH to the oxidized state (Jacobson, E L, and Jacobson, M K Meth Enzymol 280, 221–230, 1997). Finally, 1.4 ml of 1M $HClO_4$ was added to precipitate the total protein in the sample. Total time from dissolving to perchloric acid addition was less than five minutes. Samples were placed on ice for at least 10 min and centrifuged at 4° C. for 10 min at 3000 rpm. Each supernatant was collected and neutralized with 1 M KOH/0.33 M $K_2HPO_4$. The supernatants were assayed for NAD; the precipitates were dissolved in 1 M NaOH for protein measurement. All reagents for these assays were purchased from Sigma, St. Louis, Mo.

NAD content was assessed as described previously (Jacobson, E L, and Jacobson, M K Meth Enzymol 280, 221–230, 1997; Jacobson, E L et al., J Cell Physiol 99, 417–426, 1979). The NAD assay is based on the principle of enzymatic cycling between oxidized and reduced states, in which NAD is rate-limiting for a series of amplification reactions. Control groups, which received no supplemental niacin, consisted of six mice each, were compared with nine or ten mice from the groups which received niacin supplemented diets. The Bradford method (Bradford, M M, Anal Biochem 72, 248–254, 1976) was employed to determine protein concentration.

EXAMPLE 5
Statistical Analysis

Differences in primary tumor incidence between the experimental groups were analyzed by the Wilcoxon rank sum test. Analysis of the variance of the data was performed on the passive transfer results to test for a niacin treatment effect on the tumor challenge growth rate. Dunnett's test of multiple comparisons was then used to determine which treatment groups significantly differed in the rate of tumor growth. For the NAD assay, the Q test was first applied to the data to determine whether questionable values should be rejected. This test was conducted at the 95% confidence level. The data were then analyzed using the MIXED procedure in the statistical analysis program SAS 6.11. The MIXED procedure fits a variety of mixed linear models to data, and a mixed linear model is a generalization of the standard linear model, with the generalization being that the data are permitted to exhibit correlation and nonconstant variability. In this manner, it was possible to first account for differences and variability in duplicate or triplicate samples from the same mouse before the differences between each mouse in each group was compared. This procedure resulting in more precise group means than if each single value carried equal weight. Least-squares means for each group were calculated, and a multiple comparison between these means was made after applying a Tukey-Kramer adjustment for the p-values.

EXAMPLE 6

Reduction of Skin Tumor Development by Niacin Supplementation

Figure 1B:
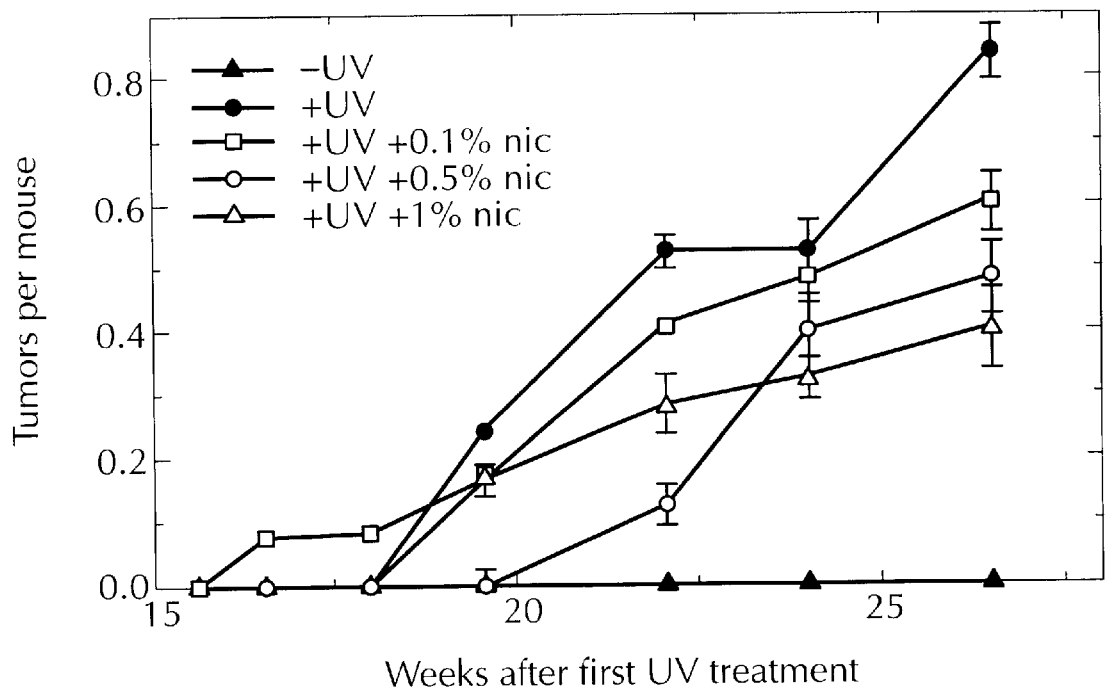

Groups of 25 mice each were fed the AIN76A rodent diet containing 10% corn oil and 30 mg niacin per kilogram diet, supplemented with 0, 0.1, 0.5, or 1.0% niacin. After three weeks of this diet, dorsally shaved mice were exposed to UV radiation for 30 min per day, five days per week for 22 weeks. This irradiation resulted in a cumulative exposure of mice to approximately $1.41 \times 10^6$ $Jm^{-2}$ of UVB radiation. Irradiated mice fed unsupplemented diets developed a 68% skin tumor incidence by 26.5 weeks after the first UV exposure (FIG. 1A). Diet supplementation with 0.1, 0.5, or 1.0% niacin reduced this incidence to 60, 48, or 28%, respectively. This dose response yielded statistically significant reduction in mice fed the 1.0% and 0.5% niacin supplemented diets (p=0.0257, Wilcoxon rank sum test). The results of the multiplicity of tumors are presented in FIG. 1B. Supplementation of the basal diet with 0.1, 0.5, or 1.0% niacin reduced the number of tumors per mouse from 0.72 to 0.6, 0.48, or 0.4%, respectively at 26.5 weeks after the first UV treatment.

EXAMPLE 7

Niacin Ingestion and Body Weights of UV-Irradiated Mice

Niacin ingestion was calculated from diet consumption recorded on 50% of the animals of each group. Unirradiated mice fed the basal diet ingested an average of 0.09+/−0.03 mg niacin per day per mouse throughout the experiment, and UV irradiated mice had a similar food intake. As shown in Table 1, UV irradiated mice fed the 0.1, 0.5, or 1.0% niacin supplemented diets had average intakes of 2.54(+/−0.56), 13.93(+/−3.3), or 28.89(+/−6.0) mg niacin per day per mouse, respectively throughout the study. These results demonstrate that there was an increased amount of niacin ingestion in mice fed higher concentrations of niacin in their food. The body weights of the UV-irradiated mice, with or without supplemental niacin, were similar (Table 1), suggesting that tumor prevention was not influenced by other nutritional factors.

TABLE I

| | Niacin Consumption | | | |
|---|---|---|---|---|
| Treatment | Food Consumed (g/mouse/day) | Dietary Niacin (g/kg diet) | Niacin Ingested (mg/mouse/day) | Body Weight (grams) |
| +UV | 2.86 (0.55) | 0.03 | 0.09 (0.02) | 18.2 (0.54) |
| +UV +0.1% Niacin | 2.47 (0.54) | 1.03 | 2.54 (0.56) | 18.2 (0.77) |
| +UV +0.5% Niacin | 2.77 (0.66) | 5.03 | 13.93 (3.3) | 18.07 (1.37) |
| +UV +1% Niacin | 2.88 (0.60) | 10.03 | 28.89 (6.0) | 18.55 (0.91) |

Values shown are means, standard deviations are shown in parentheses.

EXAMPLE 8

Influence of Niacin Suplementation on Photoimmunosuppression

The reduced ability of UVB-irradiated mice to reject syngeneic antigenic tumor cells is mediated by photoimmunosuppression. This response is measured by a passive transfer assay in which splenocytes from a UV irradiated mouse are injected into a naive unirradiated mouse (Gensler, H L and Magdaleno, M, *Nutr Cancer* 15, 97–106, 1991). The accelerated growth of tumor cells implanted in recipients of splenocytes from UV irradiated donors as compared with unirradiated donors is a measure of the amount of transferred photoimmunosuppression. The capacity of niacin supplementation to prevent photoimmunosuppression was measured in this experiment.

Figure 2:
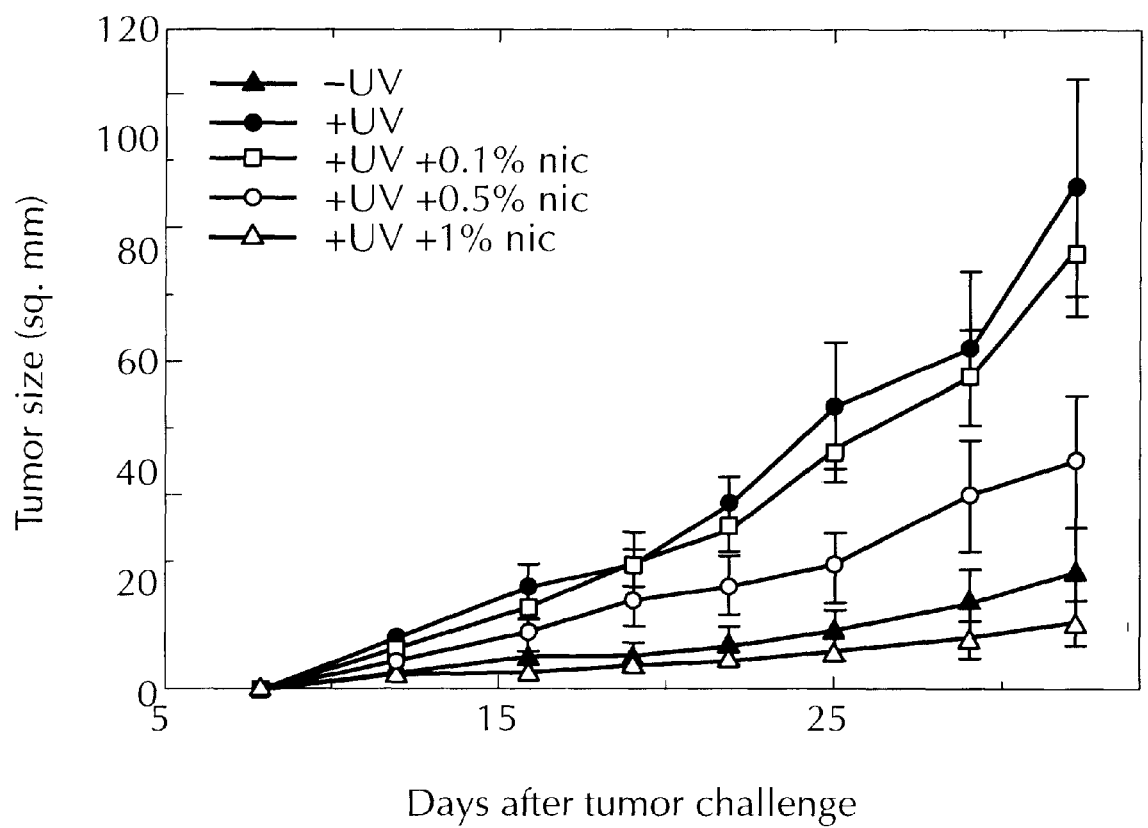
FIG. 2. depicts growth of UVM12 tumor cells in naive syngeneic mice after injection of splenocytes from UV-irradiated donors treated with niacin supplementation.

Briefly, mice were fed supplemented diets (0, 0.1%, 0.5%, or 1.0% niacin) for three weeks before UV radiation treatments began. UVB irradiation consisted of five 30 minute exposures per week for 11 weeks. Splenic leukocytes (one organ equivalent) of UV irradiated mice were injected intravenously into each of 15 naive recipients. Within 24 hours, these mice were challenged with an intradermal injection of $5 \times 10^5$ UVM12 syngeneic antigenic tumor cells. The growth of these tumor cells was measured and presented in FIG. 2. The values displayed are the mean values +/−the standard deviation. As can be seen from FIG. 2, the mean tumor size was 21.9 sq mm in recipients of splenocytes from unirradiated control mice, at 32 days after the tumor challenge. Recipients of splenocytes from UVB-irradiated mice treated with 0, 0.1%, 0.5%, or 1.0% niacin supplementation displayed mean tumor sizes of 91.6(+/−19.7), 79.8(+/−11.5), 41.9 (+/−11.7), or 13.2(+/−4.1) sq mm, respectively. Analysis of variances indicates that there was a significant treatment effect on the tumor growth rate (p=0.0001). Dunnett's test shows that the tumor challenge growth in recipients of splenocytes from UV irradiated mice treated with 0.5% or 1.0% niacin was significantly lower than that in recipients of splenocytes. This demonstrated that supplemental niacin in the range of 0.5–1.0%, prevented UV-induced photoimmunosuppression as manifested by the ability of the recipient mice to reject antigenic tumors.

EXAMPLE 9

Influence of Niacin Supplementation of Skin NAD Levels

UV exposure was directed to the dorsal shaved skin of treated mice. To assess the ability of ingested niacin to enhance NAD levels in UV irradiated as well as in unirradiated skin, both unirradiated ventral skin and dorsal UV irradiated skin were collected. For each mouse, either one, two, or three skin samples were collected at different sites form both the dorsal and ventral surfaces at 4.5 weeks post UV treatment. The samples were extracted to measure total NAD, and these values were expressed relative to protein content to normalize the data.

Figure 3A:
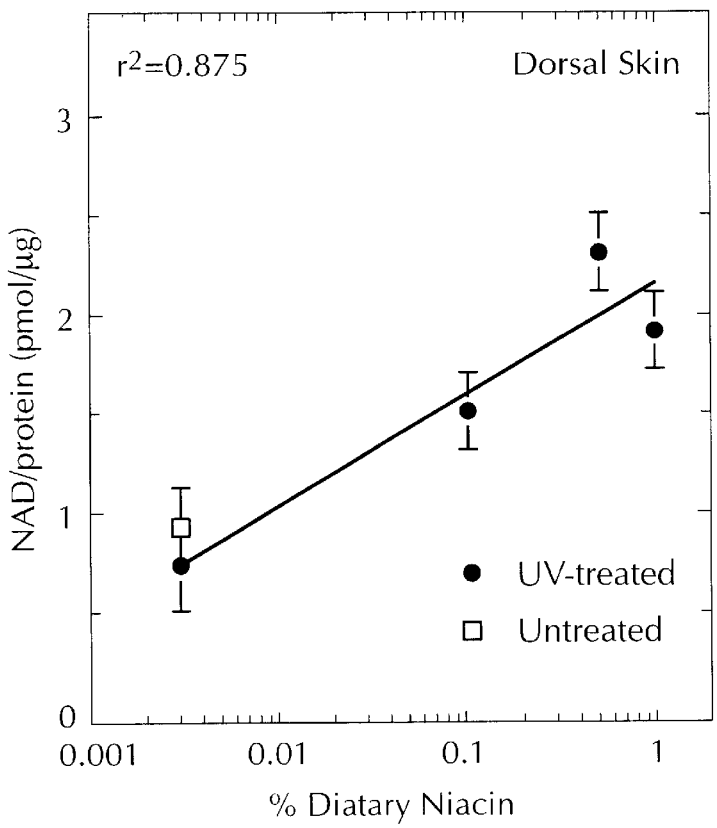
FIG. 3. depicts NAD content in dorsal (A) and ventral (B) skin of niacin-supplemented mice. Closed circles represent the average skin NAD, relative to protein, of mice that were treated with UV radiation, and an open square represents the average skin NAD, relative to protein, of unsupplemented and untreated mice. Best-fit, logarithmic curves are shown for both skin locations; error bars represent standard error.
Figure 3B:
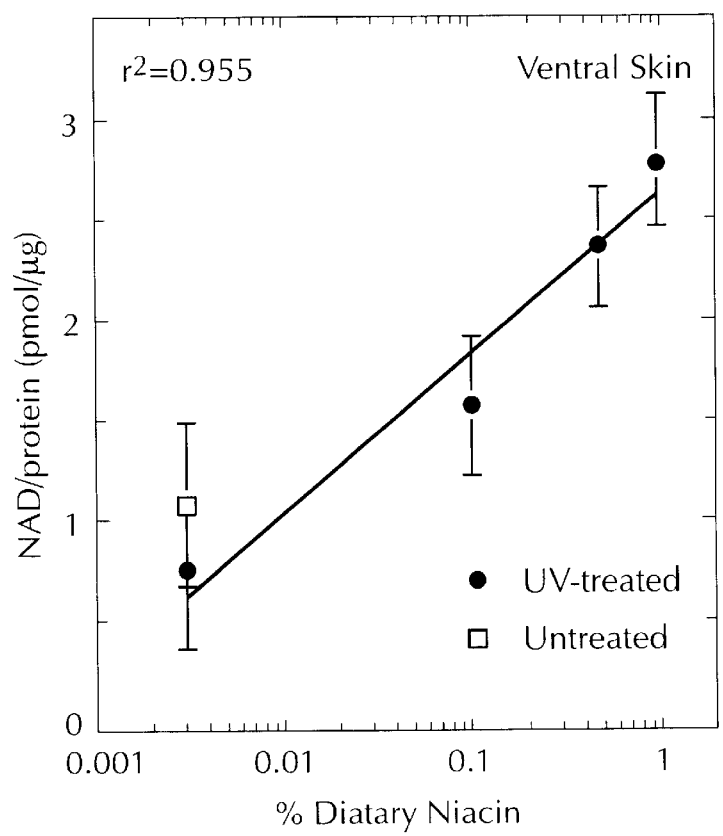

The results, shown in FIG. 3, show that niacin supplementation elevates cellular NAD. When the cellular NAD levels were plotted against the diet niacin level, it was found that the relationship of niacin concentration in the diet to NAD in skin fits a logarithmic function. This logarithmic fit suggested that NAD content approaches saturation at 0.5–1.0% niacin supplementation. UV-irradiated mice receiving 0.5 and 1.0% niacin supplementation had significantly higher skin NAD content than UV-irradiated mice receiving no additional niacin (p<0.0001 for dorsal skin, p=0.0114 for ventral skin, in 0.5% niacin supplemented mice; and p=0.0025 for dorsal skin, p=0.0017 for ventral skin, in 1.0% supplemented mice). The increase in NAD/protein ratios appears greater for the ventral skin than the dorsal skin in the 1.0% niacin group, although neither value is significantly different from values in the 0.5% niacin group. This suggests that a niacin concentration in the diet of 0.5 to 1% approach cutaneous NAD saturation.

Oral niacin administration may prevent photoimmunosuppression and photocarcinogenesis by a number of mechanisms. For example, oral niacin may modulate 1) ADP-ribose transfer reactions that are known to affect base excision repair, 2) p53 expression, which is important in nucleotide excision repair, and 3) apoptosis (Ménissier de Murcia, J et al., Proc Natl Acad Sci, USA 94, 7303–7307, 1997; Ford, J M and Hanawalt, P C et al., J Biol Chem 272, 28073–28080, 1997; Ziegler, A et al., Nature 372, 773–776, 1994.). Poly(ADP-ribose) polymerase is required in base excision repair, the pathway for repair of oxidative DNA damage, such as that induced by the UVA (320–400 nm) portion of UV radiation (Ménissier de Murcia, J et al., Proc Natl Acad Sci, USA 94, 7303–7307; Demple, B and Harrison, L, Annu Rev Biochem 63, 915–948, 1994; Kvam, E and Tyrrell, R M, Carcinogenesis 18, 2379–2348, 1997). Expression of p53 is necessary for efficient nucleotide excision repair of cyclobutane pyrimidine dimers and 6-4 photoproducts from DNA damaged by the UVC (200–280 nm) and UVB (280–320 nm) wavelengths of UV radiation (Ford, J M and Hanawalt, P C et al., J Biol Chem 272, 28073–28080, 1997; Rosentstein, B S, and Mitchell, D L, Photochem Photobiol 45, 775–780, 1987). NAD, the major metabolite of niacin, is a substrate for PARP, a nuclear enzyme which binds to, and is activated by DNA strand scissions (James, M R and Lehman, A R, Biochem 21, 4007–4013, 1982). PARP interacts with numerous proteins involved in DNA repair, including XRCCI, DNA ligase III, and p53 (Masson, M et al., Mol Cell Biol 18, 3563–3571, 1998; Vaziri, H et al., EMBO 16, 6018–6033, 1997). PARP activity can be limited by NAD concentration (Zhang, J Z et al., J Nutr 123: 1349–1355, 1993). The experiments demonstrate that niacin ingestion can determine NAD concentration in the skin, as had been previously reported in a number of human tissues (Canner, P H et al., J Am Coll Cardio 8, 1245–1255, 1986; Demple, B and Harrison, L, Annu Rev Biochem 63, 915–948, 1994). Exposure of normal human fibroblasts to UV radiation results in activation of PARP and concomitant utilization of NAD (Gensler, H L, J Cancer Res Clin Oncol 117, 345–350, 1991; Jacobson, E L et al., J Biol Chem 258, 103–107, 1983). Chinese hamster lung fibroblast cells with reduced NAD content display down-regulation of p53 levels and inability to mount a p53 response to etoposide, a topoisomerase II inhibitor that customarily results in increased p53 expression (Whitacre, C M et al., Cancer res 55: 3697–3701, 1995). This p53 down-regulation has also been demonstrated for human lung fibroblasts, skin fibroblasts, and mammary epithelial cells. P53 plays a critical role in skin squamous cell carcinogenesis, as evidenced by the presence of p53 mutations in over 90% of human squamous cell carcinomas of the skin (Brash, D E, et al., Proc Natl Acad Sci, USA 88, 10124–10128, 1991). The occurrence of these mutations in the early actinic keratotic stage of skin cancer suggests that p53 mutations are frequently an initiating step in cutaneous squamous cell carcinoma (Ziegler, A et al., Nature 372, 773–776, 1994). The p53 protein is a transcription factor which has an increased protein half-life in murine keratinocytes exposed to UVB radiation (Liu, M et al., Carcinogenesis 15, 1089–1092, 1994). One of the downstream genes activated by p53 in UVB/A irradiated keratinocytes is the WAF1/CIP 1 gene (Liu, M and Pelling, J C Oncogene 10, 1955–1960, 1995). Its gene product, $p21^{WAF1/CIP1}$, is a cyclin dependent kinase inhibitor that causes a G1 cell-cycle arrest by inhibiting the activity of the cyclin/cdK family (Xiong, Y et al., Nature 366, 701–704, 1993). It has been proposed that cell cycle arrest allows time for DNA repair before DNA replication. The p53 protein binds to DNA single strand scissions. PARP binds to the p53 protein as well as to DNA strand scissions in vivo, and the complex retains its DNA binding capacity (Vaziri, H et al., EMBO 16, 6018–6033, 1997; James, M R and Lehman, A R, Biochem 21, 4007–4013, 1982). Inhibition of PARP by 1,5-dihydroxyisoquinoline prevents p53 dependent induction of $P21^{waf1/CIP1}$ in human myelogenous leukemia cells exposed to γ-radiation (Vaziri, H et al., EMBO 16, 6018–6033, 1997), suggesting that PARP activity is required for activation of $P21^{waf1/CIP1}$ transcription by p53 protein. Deficiency of p53 is known to result in reduced nucleotide excision repair of UV-induced cyclobutane pyrimidine dimers and 6-4 photoproducts in total genomic DNA of human fibroblasts and in increased UV mutagenesis in murine fibroblasts (Ford, J M and Hanawalt, P C et al., J Biol Chem 272, 28073–28080, 1997; Yuan, J et al., Carcinogenesis 16, 2295–2300, 1995). Cyclobutane pyrimidine dimers and 6-4 pyrimidine photoproducts are produced in the DNA of cells exposed to UVB radiation (Rosentstein, B S, and Mitchell, D L, Photochem Photobiol 45, 775–780, 1987). Additionally, inactivation of p53 in mouse skin reduces the appearance of apoptotic keratinocytes generated by UVB irradiation (Ziegler, A et al., Nature 372, 773–776, 1994). The apoptotic killing of cells containing extensive UV-induced DNA damage is thought to remove precancerous cells from the skin. These activities of p53 suggest that down-regulation of the p53 response to UV irradiation by NAD deficiency could lead to reduced induction of $p21^{waf1/CIP1}$, decreased cell cycle arrest, decreased nucleotide excision repair, increased mutagenesis, and decreased apoptosis of severely UV-damaged cells, all resulting in enhanced photocarcinogenesis.

As a substrate for PARP, decreased NAD may influence repair of oxidative DNA damage induced by sunlight. The longer UV wavelengths, above 334 nm and near visible radiations, cause extensive oxidative DNA damage (Kvam, E and Tyrrell, R M, Carcinogenesis 18, 2379–2348, 1997). Many DNA base damages generated by oxidative processes, ionizing radiation, or by simple alkylating agents are corrected by base excision repair (Klungland, A and Lindahl, T, EMBO 16, 3341–3348, 1997; Seeberg, E et al., Trends Biochem Sci 20, 391–397, 1995; Demple, B and Harrison, L,

*Annu Rev Biochem* 63, 915–948, 1994). PARP has been implicated in the base excision repair pathway in vivo since PARP knockout mice are highly sensitive to alkylating agents and to γ-radiation (Ménissier de Murcia, J et al., *Proc Natl Acad Sci*, USA 94, 7303–7307, 1997). By binding to DNA strand scissions and to base excision repair proteins XRCC1, DNA polymerase β, and DNA ligase III, PARP detects DNA strand breaks and is thought to recruit proteins to form a multiprotein repair complex to process the strand scissions (Masson, M et al., *Mol Cell Biol* 18, 3563–3571, 1998). Niacin supplementation may also protect against oxidative DNA damage by acting as an antioxidant (Kamat, J P and Devasagayam, T P, *Chem Biol Interact* 99, 1–16, 1996).

In summary, our results demonstrate that niacin supplementation inhibits photocarcinogenesis and photoimmunosuppression in mice. Furthermore, ingestion of niacin leads to increased levels of NAD in skin. This increase was evident even in skin which had been repeatedly exposed to UV radiation (an agent known to enhance NAD consumption). These results suggest that prevention of skin carcinogenesis by supplemental niacin results from blockage of both UV-induced photoimmunosuppression and of cutaneous NAD depletion. Maintenance of NAD levels in skin with consequent PARP enhancement of base excision repair or UV induced oxidative DNA damage likely contributes to the skin cancer prevention capacity of supplemental niacin.

Other embodiments and uses of the invention will be apparent to those skilled in the art from consideration of the specification and practice of the invention disclosed herein. All U.S. patents and applications and other references noted herein are specifically incorporated by reference. The specification and examples should be considered exemplary only with the true scope and spirit of the invention indicated by the following claims.

We claim:

1. A method for inhibiting photocarcinogenesis or photoimmunosuppression in a subject comprising administering a pharmaceutical composition consisting essentially of niacin to a subject in need thereof wherein said niacin is in an amount effective to inhibit photocarcinogenesis or photoimmunosuppression in said subject.

2. The method of claim 1, wherein said subject is a mammal.

3. The method of claim 2 wherein said mammal is a human.

4. The method of claim 1, wherein said administration comprises between about 1 mg niacin per kilogram of subject weight to about 100 mg per kilogram of subject weight.

5. The method of claim 1, wherein said administration comprises between about 10 mg niacin per kilogram of subject weight and about 40 mg per kilogram of subject weight.

6. The method of claim 1, wherein said photocarcinogenesis or photoimmunosuppression is by sunlight or ultraviolet radiation.

7. The method of claim 1, wherein said pharmaceutical composition further comprises a pharmaceutically acceptable carrier.

8. The method of claim 1 wherein said pharmaceutical composition comprising niacin is administered orally to said subject.

9. The method of claim 1, wherein the subject will be exposed to a photocarcinogenic agent.

10. The method of claim 1, wherein the subject will be exposed to a photoimmunosuppresive agent.

* * * * *